United States Patent
Pittam et al.

(10) Patent No.: US 9,568,407 B2
(45) Date of Patent: Feb. 14, 2017

(54) APPARATUS, SYSTEM AND METHODS FOR DETERMINING THE IMPACT ATTENUATION OF A SURFACE

(71) Applicants: Bradley A. Pittam, Bristol, WI (US); Christopher A. Hanson, Lansing, IL (US); Michael Hanson, Plainfield, IL (US)

(72) Inventors: Bradley A. Pittam, Bristol, WI (US); Christopher A. Hanson, Lansing, IL (US); Michael Hanson, Plainfield, IL (US)

(73) Assignee: Sonam Technologies, LLC, Lake Forest, IL (US)

( * ) Notice: Subject to any disclaimer, the term of this patent is extended or adjusted under 35 U.S.C. 154(b) by 0 days.

(21) Appl. No.: 14/704,738

(22) Filed: May 5, 2015

(65) Prior Publication Data

US 2015/0338327 A1    Nov. 26, 2015

Related U.S. Application Data

(60) Provisional application No. 61/988,664, filed on May 5, 2014.

(51) Int. Cl.
| | | |
|---|---|---|
| *G01M 7/00* | (2006.01) |
| *G01N 3/48* | (2006.01) |
| *G01N 3/303* | (2006.01) |
| *E01C 13/00* | (2006.01) |
| *G01L 5/00* | (2006.01) |
| *G01P 15/00* | (2006.01) |

(52) U.S. Cl.
CPC ............. *G01N 3/48* (2013.01); *E01C 13/00* (2013.01); *G01L 5/0052* (2013.01); *G01N 3/303* (2013.01); *G01P 15/00* (2013.01)

(58) Field of Classification Search
CPC .......... G01N 3/303; G01N 3/30; G01N 3/40; G01N 3/00; G01M 7/08; G01L 5/00
USPC ................... 73/12.13, 12.09, 12.01, 78
See application file for complete search history.

(56) References Cited

U.S. PATENT DOCUMENTS

| | | | | |
|---|---|---|---|---|
| 4,856,318 A * | 8/1989 | Hogan | ............... | G01N 3/303 73/12.13 |
| 5,736,631 A * | 4/1998 | Dixon | ............... | G01N 3/307 73/12.06 |
| 2006/0135854 A9* | 6/2006 | McDonough | ........ | A61B 5/0002 600/300 |
| 2007/0277584 A1* | 12/2007 | Fischer | ............... | B60R 21/01 73/1.01 |
| 2013/0055797 A1* | 3/2013 | Cline | ............... | G01N 3/303 73/82 |

* cited by examiner

*Primary Examiner* — Lisa Caputo
*Assistant Examiner* — Nigel Plumb
(74) *Attorney, Agent, or Firm* — Patzik, Frank & Samotny Ltd.

(57) ABSTRACT

The instant disclosure relates to an apparatus, system and methods for determining the impact attenuation or hardness of a surface for a playground or sports field in order to mitigate or reduce sports and playground related injuries.

7 Claims, 13 Drawing Sheets

Impact Analyzer 1.2
TEST INPUT SCREEN

Customer:       Kenosha Unified School District

Location:       Arick Henry Elementary School

Playground:     North

Surface Type:

Engineered Wood Fiber
    Wood mulch
    Poured in place/unitary rubber
    Rubber mulch
    Rubber tiles
    Artificial turf over foam pads
    Artificial turf over loose rubber
    Grass
    Sand
    Dirt
    SMARTE System
    Other Surface Depth: 12"

Fig. 8A

Impact Analyzer 1.2
NEW LOCATION SET UP SCREEN

Customer: Kenosha Unified School District

Location: Arick Henry Elementary School

Playground: North

Surface Type:

Engineered Wood Fiber
    Wood mulch
    Poured in place/unitary rubber
    Rubber mulch
    Rubber tiles
    Artificial turf over foam pads
    Artificial turf over loose rubber
    Grass
    Sand
    Dirt
    SMARTE System
    Other

Surface Depth: 12"

Fig. 8B

Impact Analyzer 1.2

Location:        Lake Forest, IL
Surface:         Engineered Wood Fiber
Surface Depth:   12"
Fall Height:     6' 2"
Drop Angle:      90°
HIC/GMAX:        607/115
Test ID:         ZZ44365

Safety Risk Levels

Minor Brain Injury                90%

Moderate Brain Injury             54%

Critical Brain Injury             1%

Fatality                          0%

<u>Test Taken</u>

| Time | Date | Temp |
|------|------|------|
| 9:10AM | Feb 18, 2014 | 14F |

Fig. 9A

Impact Analyzer 1.2

Location:      Lake Forest, IL
Surface:       Rubber Mulch
Surface Depth: 6"
Fall Height:   6' 2"
Drop Angle:    90°
HIC/GMAX:      200/50
Test ID:       ZZ44128

Safety Risk Levels

Minor Brain Injury             22%

Moderate Brain Injury          8%

Critical Brain Injury          0%

Fatality                       0%

<u>Test Taken</u>

| Time | Date | Temp |
|------|------|------|
| 8:55AM | Feb 18, 2014 | 14F |

Fig. 9C

Impact Analyzer 1.2
Location:     Lake Forest, IL
Surface:      Engineered Wood Fiber
Surface Depth: 12"
Fall Height:  6' 2"
Drop Angle:   90°
HIC/GMAX:     1800/307
Test ID:      ZZ44541
Safety Risk Levels
Minor Brain Injury                100%
Moderate Brain Injury             100%
Critical Brain Injury             45%
Fatality                          10%
Test Taken
| Time | Date | Temp |
|---|---|---|
| 9:22AM | Feb 18, 2014 | 14F |
Fig. 9D

APPARATUS, SYSTEM AND METHODS FOR DETERMINING THE IMPACT ATTENUATION OF A SURFACE

CROSS-REFERENCE TO RELATED APPLICATION

This application claims the benefit of U.S. provisional application Ser. No. 61/988,664, filed May 5, 2014, which is hereby incorporated by reference in its entirety.

BACKGROUND OF THE INVENTION a. Field of the Invention

The instant disclosure relates to an apparatus, system and methods for determining the hardness of a surface, and in particular, the instant disclosure relates to a device, system and methods for determining the impact attenuation or hardness of a surface for a playground or sports field in order to mitigate or reduce sports and playground related injuries.

b. Background Art

In the United States alone, over 100,000 children go to the emergency room every year because of a fall onto a playground safety surface, which represents over 50% of all playground injuries. Between 1999 and 2000, 31 children died as a result of a fall onto the safety surface. Equally concerning is that brain injuries for this group continues to be on the rise since 2004 with over 110,000 children age 14 and under suffering a sports related traumatic brain injury. In 2012 nearly 4,600 children in the United States under the age of five suffered from a traumatic brain injury on the playground. While United States statistics are reported herein, this is a worldwide issue.

In an attempt to prevent these injuries, some playground owners install and maintain an impact attenuating safety surface in the use zone of the playground area. However, playground owners need data to assess which playground safety surface to use prior to purchase as well as, more importantly, data on how their safety surfacing is performing in use.

In the United States, it is estimated that there about 200,000 playgrounds at schools and local parks. These playgrounds are owned and operated by approximately 17,600 school districts and 9,900 city, county, state and federal park districts. Commonly there is overlap between these two segments for playground ownership and maintenance whereas the local park district will maintain and/or own the schools' playground.

According to Certified Playground Safety Inspector (CPSI) training, ASTM standards and Consumer Product Safety Commission guidelines, playground owners are to install and maintain impact attenuating surfaces in the use zones around playground equipment. As an example, ASTM F1292, titled Standard Specification for Impact Attenuation of Surfacing Materials Within the Use Zone of Playground Equipment, establishes minimum performance requirements for the impact attenuation of playground surfacing materials installed within the use zone of playground equipment. ASTM F1292 is incorporated herein by reference.

Additionally, CPSI training recommends playground owners inspect and maintain the playground surface and keep maintenance logs proving the surface was inspected and maintained to provide critical fall height protection. However, playground owners lack a quick, cost effective and convenient way to assess the impact attenuation provided by the safety surface as part of the routine playground maintenance schedule. Therefore, most playground owners and CPSIs can only report that the surface was visually inspected and maintained to a certain depth but they cannot routinely test and verify in the field that it is providing sufficient impact attenuation to prevent injuries.

Today, the safety of a playground surface is determined by assessing its risk to generate a Critical Brain Injury at a given fall height. This is done by conducting a test set out in ASTM Standard F1292, and in particular ASTMF1292-13, all of which are incorporated by reference herein. This test primarily utilizes a Triax2010 manufactured by Alpha Automation to determine the critical fall height of a playground safety surface. Similarly, in Europe, the test standard is the EN1177, incorporated by reference herein.

However, the current test equipment is prohibitively expensive for mass market use and the level of acceptable injury risk allowed from a fall onto a playground safety surface is outdated. Today, in large part, playground owners unknowingly subject children to high risk levels of a fatality or Critical Brain Injury should they fall, and they lack a quick, convenient method to assess that risk.

Because the current test equipment is too expensive for a playground owner to purchase and maintain and too cumbersome and fragile for frequent use, most playground safety surfaces are evaluated in a lab prior to purchase and installation, instead of in the playground once it is installed and in use.

The level of acceptable risk allowed during a fall onto a playground safety surface is severely outdated and other industries have taken great steps to limit risks. A playground safety surface is deemed safe and acceptable if it generates a Head Injury Criterion (HIC) value of 1,000 or less. A 1,000 HIC translates into a 2% risk of a fatality and an 8% risk of a non-recoverable brain injury as a result of a fall onto the surface.

The automobile industry provides a much safer environment for its occupants. For example, for a car to earn a "Good" rating in a NHTSA 40 MPH front offset crash, the HIC cannot exceed 560. For a car to earn a "Poor" rating the HIC cannot exceed 840, as compared to a 1,000 HIC allowed on a playground. For comparison, a 500 HIC translates into a 0% risk of a fatality and a 2% risk of a non-recoverable brain injury.

As such, there is a need for a cost effective and convenient solution for playground owners to assess the impact attenuation of the surfacing materials and keep a maintenance log of those assessments. The instant disclosure provides such advantages and solutions.

BRIEF SUMMARY OF THE INVENTION

While not every injury can be prevented, playground and sports filed injuries can be greatly reduced if playground and sports field owners have immediate, easy to understand data about the impact protection their surface is providing. The present disclosure provides playground and sports filed owners a convenient and cost effective device to accurate and quickly obtain data pertaining to the impact attenuation of the surface in question.

As other markets have learned from available head impact data and implemented positive changes to improve safety, the playground market is anticipated to follow suit. The maximum HIC should be reduced from 1,000 down to at most 700. Once this change is accepted, and the Consumer Product Safety Commission adopts the change, playground owners will need to update their playground safety surfaces to comply with the current guidelines—creating a demand for a quick, reliable, accurate and cost effective field test method. The impact tester disclosed herein solves this data acquisition need.

Accordingly, one objective of the present disclosure is to provide an apparatus that can be used on a playground or sports field surface to determine the hardness or the impact attenuation of the surface by dropping the apparatus at different locations on the playground or sports field, while relevant data is automatically recorded and stored in the device or automatically transmitted from the apparatus to a receiving device, where it is recorded and stored for future reporting.

Another objective of the present disclosure is to provide an apparatus in the shape of a ball that can be used on a playground or sports field surface to determine the hardness or the impact attenuation of the surface by dropping the ball at different locations on the playground or sports field, while data is automatically determined, collected, stored and/or transmitted to a receiving device, such as a smart phone, tablet or laptop.

Yet another objective of the present disclosure is to provide a system and methods for determining the hardness or the impact attenuation of the surface of a playground or sports field by dropping a device onto the surface at different locations. Data pertaining to the hardness of the surface is automatically determined, collected, stored and/or transmitted from the device to a receiving device, where the data is determined, collected and/or stored for reporting purposes.

Other objects and advantages of the present disclosure will become apparent to one having ordinary skill in the art after reading the specification in light of the drawing figures, however, the spirit and scope of the present disclosure should not be limited to the description of the embodiments contained herein.

BRIEF DESCRIPTION OF THE DRAWINGS

FIGS. 8A and 8B show exemplary screens for an HMI display for testing the hardness or impact attenuation of a surface in accordance with the present disclosure.

FIGS. 9A through 9D show exemplary screens for an HMI display for testing the hardness or impact attenuation of a surface in accordance with the present disclosure.

DETAILED DESCRIPTION OF THE INVENTION

Figure 1:
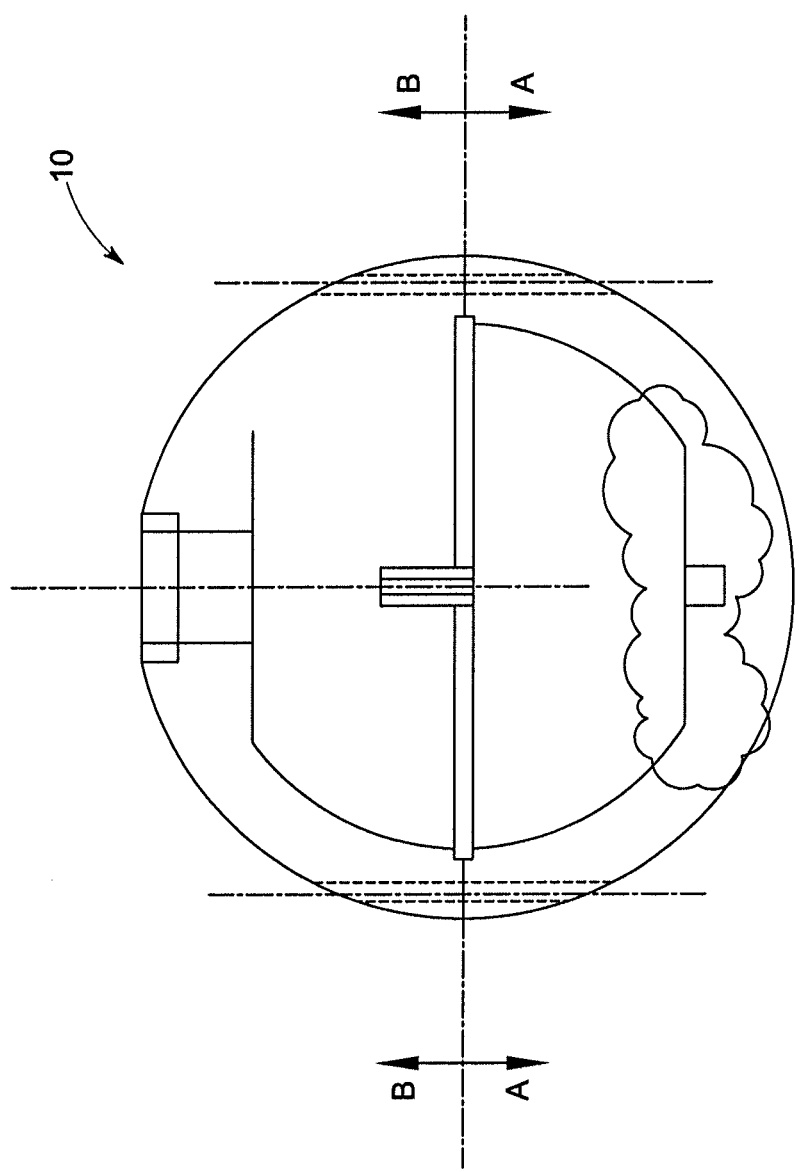
FIG. 1 is a perspective view of a device for testing the hardness or impact attenuation of a surface in accordance with the present disclosure.
Figure 2:
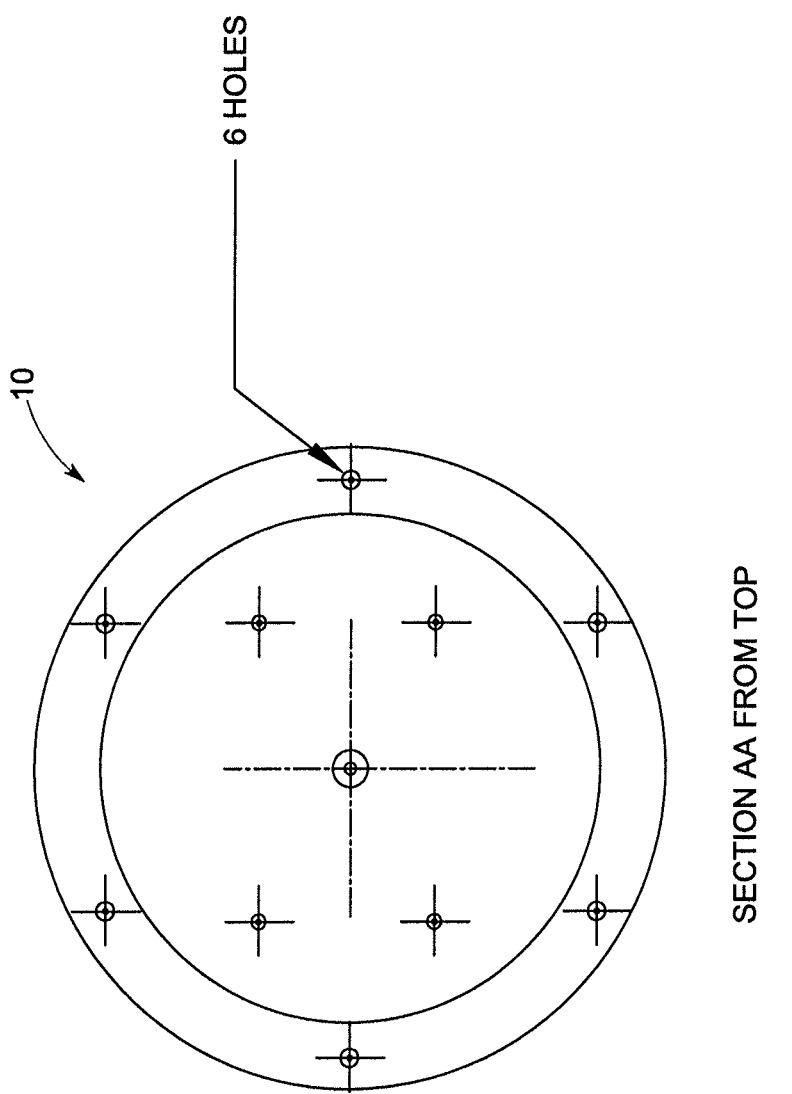
FIG. 2 is a perspective view of a device for testing the hardness or impact attenuation of a surface in accordance with the present disclosure.
Figure 3:
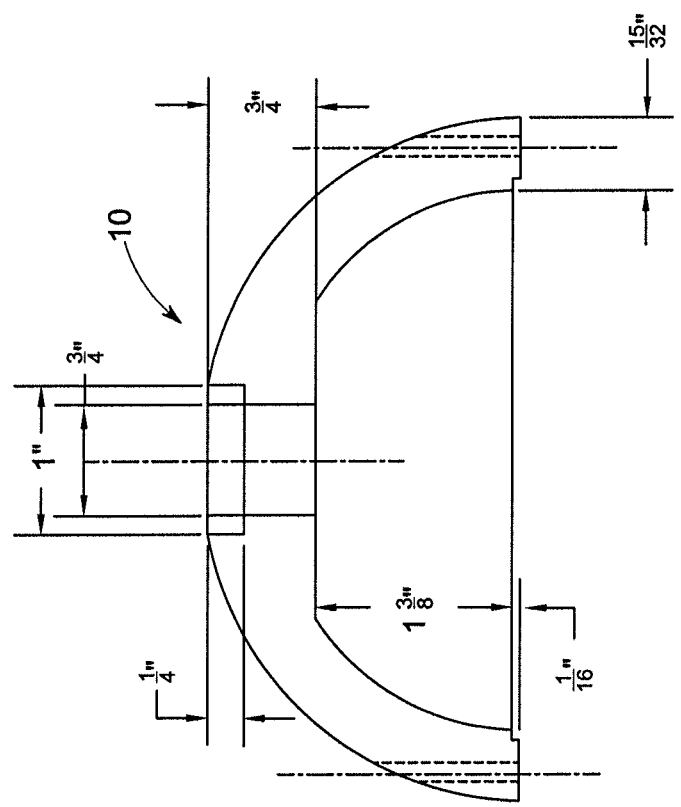
FIG. 3 is a perspective view of a device for testing the hardness or impact attenuation of a surface in accordance with the present disclosure.
Figure 4:
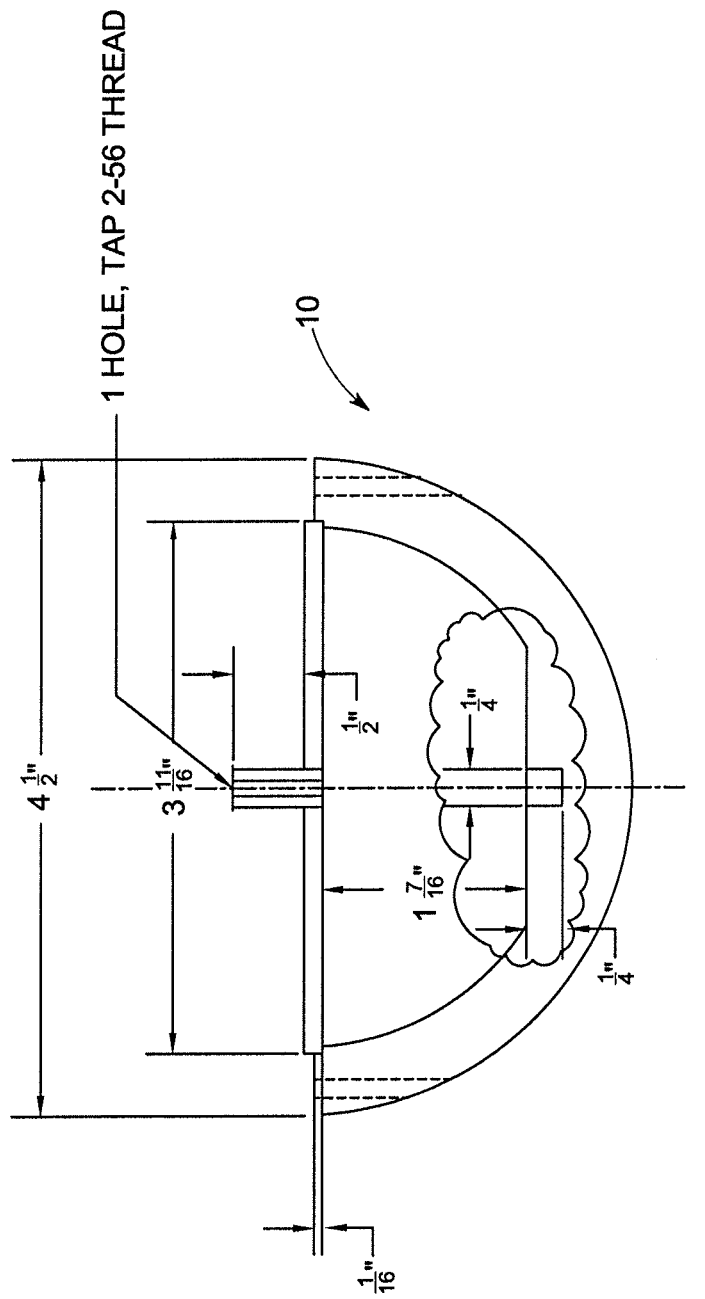
FIG. 4 is a perspective view of a device for testing the hardness or impact attenuation of a surface in accordance with the present disclosure.
Figure 5:
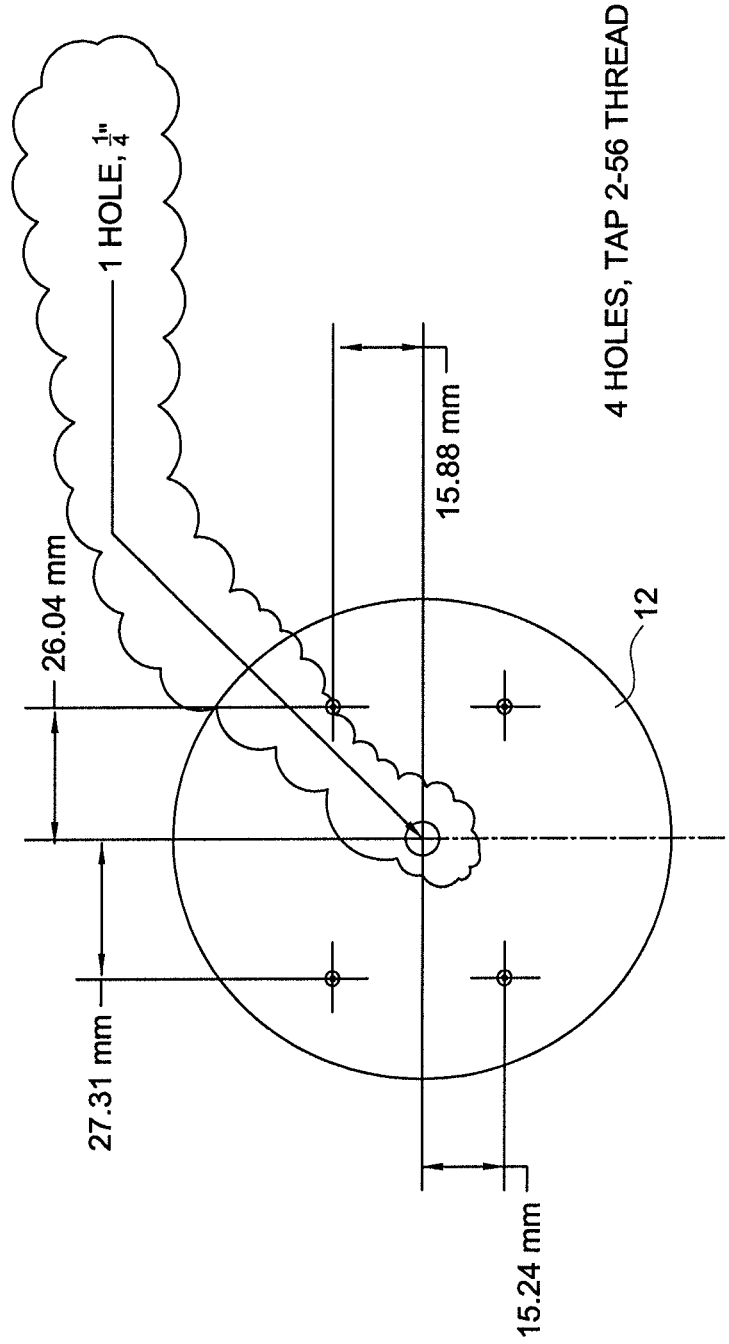
FIG. 5 is a perspective view of a mounting plate to be used in a device for testing the hardness or impact attenuation of a surface in accordance with the present disclosure.

FIGS. 1-5 of the present disclosure show an impact tester 10 for testing the hardness or impact attenuation of a surface in accordance with the present disclosure. The proprietary hardware and software technology incorporated in the impact tester 10 allows playground owners to have an easy, accurate and affordable tool to assess how much head impact protection their playground surface is providing. The impact tester 10 collects and tracks some or all of the following data points for various locations of the playground or sports field surface for each point tested: type of surface tested, depth of the safety surface, Head Impact Criteria (HIC) score, maximum acceleration during an impact event (GMAX), GPS location, fall height, fall angle, rotation, fall speed, surface temperature and weather conditions, among others.

This data is used to understand how safe the surface is in current conditions, allowing the user to determine if the playground is safe for use or if corrective action is required. In a matter of minutes, a playground owner can use the impact tester 10 to test all relevant locations within the playground or on a sports field. By using the impact tester 10, testing can be done at different playgrounds and can be used as a part of a regular maintenance program. This immediate wealth of information is not conveniently and affordably available today.

The impact tester 10 can also be used to detect HIC and GMAX at any angle of impact, which is particularly important when assessing the risk of long bone injuries.

When used as part of the playground owner's routine maintenance program, data collected from the impact tester 10 provides proof to the community that the surface is providing sufficient protection for its users. With this accurate and reliable data now included in the playground owners maintenance logs, which may be held securely by a different company for security and authenticity purposes, litigation and claims can be reduced or more accurately responded to, as the playground owner can now provide proof that the surface was properly maintained to provide sufficient impact attenuation for the play area, and that the injury was more likely accident as opposed to negligence of the playground owner to properly maintain the surface.

In the preferred embodiment, a third party (not shown) maintains a database of all tests conducted with the impact tester 10. As part of a rental and ownership user agreement, all impact data can be sent to and maintained by third party, and located on third party servers (not shown), as understood by one having ordinary skill in the art. The data can be sent securely through various transmission protocols including, but not limited to, wired or wireless transmission, cellular, Wi-Fi, Bluetooth, ZigBee, etc.

The independent, third party data collection ensures safe and responsible storage of the data. This data can be used to assist insurance companies, playground equipment companies, playground designers and playground owners in making educated decisions on surfacing using real world data instead of lab data based on ideal conditions. Playground surfacing manufacturers can use this data to analyze the performance of their surfacing systems over several years of use, in varying weather conditions and climates. Alternatively, the system can be configured so that the owner of the playground or impact tester 10 can store the data without the need for a third party server and/or storage facility.

In the preferred embodiment, the impact tester 10 is a battery-powered, portable, handheld, spherical device used to determine the impact attenuation properties of a given material, such as a playground. The impact tester 10 can be made of many durable materials, and in the preferred embodiment is made of carbon steel and is made from two separate semi-sphere portions that are attached to each other with screws or any other fastening devices and contain a mounting plate 12 (shown in FIG. 5). The mounting plate 12 secures and holds a printed circuit board containing the components set out in FIG. 7. The tester 10 can be configured as other shapes as well, such as an oval shape or a missile shape, etc. The tester 10 may be configured with a bus, 210, at least one processor 220, a memory 230, an I/O interface 250, a communications interface 260, and a GPS chip 270, depending on the particular functions of the tester 10 and as described below with reference to FIG. 7.

In the preferred embodiment, one to four surface mounted MEMS accelerometers 240 will monitor acceleration and rotation of the tester during an impact event. This data (along with geographic location, temperature, and rotation) will be relayed via Bluetooth, or some other transmission protocol, back to a human machine interface (HMI) 20. The HMI 20 can be a computer, tablet computer, personal digital assistant PDA, or a cell phone running an application program, among others.

The hardware and software package incorporated into the impact tester 10 and/or the software in the HMI will calculate HIC, fall height, GMAX, maximum velocity and angle of impact based on these inputs, as described herein, using the onboard sensors 240.

As described herein, the Head Impact Criteria (HIC) score is determined for a given surface that the impact tester 10 is dropped onto for testing. Among ways the HIC score can be determined is the standard disclosed in ASTM F1292, Section 9.5, and in particular, the calculation set out in Section 9.5.2.

The Fall Height is the vertical distance the impact tester 10 fell before impact. The accelerometers 240 in the impact tester 10 will determine the time when the tester 10 is dropped and starts to fall, and when it first impacts the ground, and it will use this time to determine the fall height, i.e., $\frac{1}{2} Gt^2$, where time t is in seconds, G is the gravitational constant 32.15 ft./s².

The maximum velocity at impact can be determined by the peak velocity during the drop and can be calculated by multiplying fall time by gravity, or v=Gt, where velocity expressed in feet per second and again G=32.15 ft./s² and time is in seconds. As understood by one having ordinary skill in the art, this equation can be converted to miles per hour with the following equation:

v(60)(60)/5280, where velocity expressed in feet per second.

Other calculations performed by the accelerometers 240 include the angle of impact, which is the angle at which the impact tester 10 impacts the surface of the playground; the GMAX, which is the maximum acceleration during the impact event; and the rotation of the device during the impact event. Further, the location is the geographical location of the test, which is determined by the GPS chip 270, included in the hardware. Finally, the ambient temperature is determined using third party data, that can be accessed in a number of different ways including a weather application on the phone, tablet or computer. Weather information can also be obtained from a sensor (not shown) on the tester 10.

Figure 6A:
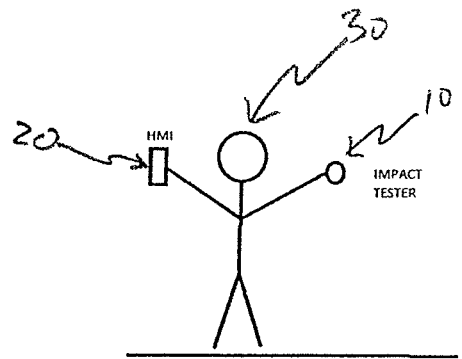
FIG. 6A is a drawing of the impact tester device in use for testing the hardness or impact attenuation of a surface in accordance with the present disclosure.
Figure 6B:
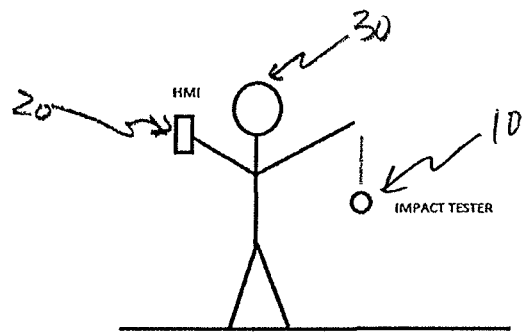
FIG. 6B is a drawing of the impact tester device in use for testing the hardness or impact attenuation of a surface in accordance with the present disclosure.
Figure 6C:
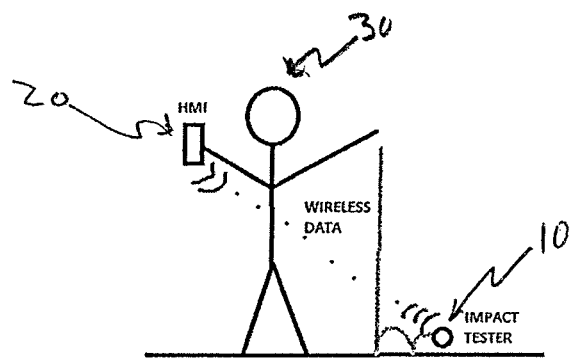
FIG. 6C is a drawing of the impact tester device in use for testing the hardness or impact attenuation of a surface in accordance with the present disclosure.

In general terms, the operation of the device can be done using the following steps, although different steps or even these steps in a different order is as follows:
1. an operator or user 30 selects a location to test;
2. the operator or user 30 turns on the power of the impact tester 10;
3. the operator or user 30 turns on or enables the HMI 20;
4. as shown in FIG. 6A, the impact tester 10 is ready to be dropped and the HMI 20 is ready to receive the data;
5. as shown in FIG. 6B, the operator or user 30 then drops the impact tester 10 on the surface from the height to be tested;
6. As shown in FIG. 6C, the impact tester 10 strikes the surface and transmits data back to the HMI 20, which records the incoming data, makes necessary calculations and stores and displays the desired outputs.

The software or computer code can be located in the impact tester 10, the HMI 20 or in the preferred embodiment, some combination of both the impact tester 10 and the HMI 20. In the preferred embodiment, the impact tester 10 records data and then transmits that data to the HMI 20, however, the tester 10 can be configured to record data, calculate and store the original and resulting data. The HMI 20 contains software, through an application, to receive the data from the impact tester 10, make the necessary calculations, store and display the data.

In the preferred embodiment, the HMI 20 utilizes a welcome or start up screen for when the application software is accessed by the user or operator 30. A top level menu allows the user 30 to access various functions of the system to run the tests. The menu may contain one or more of the following functions:
a) connect the impact tester 10, in which an application on the HMI 20 can verify connectivity with the impact tester 10;
b) upload drop test data to the server, in which when Wi-Fi connectivity is available (or some other communication functionality exists), test data can be uploaded to a database, which in the preferred embodiment is a remote database maintained by an independent third party. The access to this function can be password protected for security reasons and for authentication purposes;
c) conduct drop tests, in which the test process is initialized and checked to ensure that the impact tester 10 is operating properly, communicating with HMI 20 properly, is properly orientated, and ready for the initial drop/test;
d) view drop test results, as shown by example only in FIGS. 9A through 9D, in which a visual output of a single test and/or all tests performed is provided for a given site;
e) administration and/or maintenance, which is also password protected; and
f) settings, which is used to generate or modify the system settings.

The menus and descriptions for each of the functions described above are set forth below. The user accesses the "connect to the tester" functionality for the following tasks:
a) find all the testers in range. The HMI 20 and the associated application software will search for all test devices in a given range;
b) select a tester. When multiple test devices are being used within the same range, the user is prompted to select a particular impact tester 10. The impact tester 10 selection can be via serial number or some other identification differentiator;

c) connect with the selected tester. The HMI 20 is prompted to establish a link to selected impact tester 10; and d) check tester status/systems test. Diagnostic function in which the HMI 20 checks connectivity and prompts the impact tester 10 to run system diagnosis to ensure proper function, battery level, and all other pre-requisites for conduction drop test.

Next, the drop test can be performed with the following tasks:

a) Calibration Drop Test. A test can be performed on a test mat with a known HIC value at a specified height, or other known data. The test measures whether the impact tester 10 is operating within acceptable tolerances, for example, within 5%. If the impact tester 10 is within limits, continue, and if the impact tester 10 is out of limits, test again. If the impact tester 10 fails on the second calibration drop test, the device must be returned to manufacturer for repair and analysis.

b) Site Selection.
  i. select location (manual entry of main location; address, school name, park name, etc.) This is the primary location designation and could be a street address, name of a park or school or any other primary designation for the location of the testing;
  ii. select type of environment field/park/school (manual entry or drop down menu). This function allows the user to designate a specific environment within the primary location designation;
  iii. select sub-location (which sports field, which playground at the site if applicable). This function allows the user to designate a sub-location within the primary location. Sub-designations should be used where multiple sites within a primary location are present. Designation syntax can be by name, orientation to the site (North, South, East, West, etc.) or any manual entry that uniquely identifies the sub-location;
  iv. select the sub-type of site being tested (soccer field, football field, multipurpose field, other field, 0-5 playground, 5-12 playground, 0-12 playground, other playground, other type of surface. Manual entry or drop down menu). This function allows the user to designate the environment being tested based on logical assumptions of primary use;
  v. Select surface type (manual entry or drop down menu). This function designates the primary type of surface being used within the site being tested. If multiple surfaces are present then a separate test should be used for each with proper designation and identification;
  vi. select installation depth of surface (manual entry or drop down menu). This function identifies the current installed depth of the surface system or thickness of surface in the case of unitary surface systems (non-loose fill); and
  vii. select original installation date or last maintenance date if known (manual entry). This function designates the original installation date for the surface system and/or last date that maintenance was performed if known. Once the information is entered, it can be accessed by display or report to indicate to the user the specific information as shown in FIGS. 8A and 8B.

c) Begin Test
  i. power up impact tester 10. There is a power button (not shown) located on exterior of the tester on the top hemisphere;
  ii. verify impact tester 10 is ready to be dropped. After power up, the impact tester 10 runs internal diagnostic to ensure that it is properly functioning, batteries are charged, etc.
    1. green LED is good;
    2. red LED is bad.
  iii. drop tester at desired test site. After selection, the user is ready to perform the drop test per the recommended guidelines;
  iv. see results. After drop test, the user can visually see the results of the test to look or anomalies versus expected results;
    1. accept test. If test is accepted, the data will be stored until all drop tests at given site are complete. At that point the test will close out and operator will have the option of moving on to next site or surface type within a site;
    2. delete test (angle could be off, user could have thrown the impact tester 10, hit something on the way down, etc.)

d) End Tests (on surface at specified site). After all tests on a given surface at a specified site have been performed the user will have the option of closing out the test, selecting another surface type at the same location, or selecting another sub-location at the primary location for additional tests if applicable;
  i. continue tests for new surface at same playground (go to surface selection entry page);
  ii. continue for new playground at same school/park (go to sub-location/subtype function);
  iii. end all tests.

Next, the drop test data can be uploaded by utilizing the following tasks:

a) verify Wi-Fi (or other transmission protocol) connection is established. If Wi-Fi connectivity is available, the data can be uploaded to the a database (as described herein) for later retrieval and report generation;

b) connect, login to server by way of customer User ID and Password;

c) upload data to desk top/laptop and database;

Next, the administration and maintenance functions can be accessed. This function is password protected and is used for data management and to delete data when necessary.

Finally, the settings can be accessed for the following tasks:

a) color modes, including day time, night time, color schemes;

b) connect to a different tester;

c) enter user name and password;

d) Bluetooth pairing and Wi-Fi WEP key entering would be entered and stored via hand held operating system;

e) set up and/or modify test sites;
  i. enter city name;
  ii. enter park/school/field name;
  iii. enter playground name/description.

As described herein, the HMI 20 can be a smart phone, tablet, PDA, desktop computer or laptop. To access and run the HMI 20 software or application, the user first receives a startup screen on the particular device. The user must login and provide a proper password for access to the application. The user will then be prompted to either link wirelessly to the hand held device to upload test data or link to the third party database for retrieval of test data. If the user has previously uploaded test data from the HMI 20 then that data can be retrieved from the database for report processing. The user can also retrieve other sets of test data from the database as well.

If the user chooses to upload data from the impact tester 10 to the desktop or laptop, the data uploaded will also be sent to the third party database for storage.

Data from selected sites and/or times can be formatted for printed output and/or to save on the user's hard drive. Stock reports can have output similar to the HMI 20 screen output, or the reports can be customized for a particular user's needs.

As described herein, the database server can be securely kept by a third party or by the user. To the extent a third party has possession of the database server, the authenticity of the data can be more easily established. Regardless, registered users can access their data on an unlimited basis, and any user can access the complete database for queries in order to perform more in depth analysis on a fee based basis. The system can be set up so that all data will be anonymous with the exception of a general zip code designation, thereby allowing reports to be created for similar surfaces without knowing the particular location.

Data can be stored in any of a number of formats, however in the preferred embodiment, data is stored in the following format (per drop within a series of drops, for test location):
  a) Registered User ID;
  b) Device serial number;
  c) Date and time;
  d) Primary/main location (manually entered during test);
  e) Primary use of location (playground, sports field, etc.);
  f) Sub-location at main location if applicable;
  g) Sub-type of location if applicable;
  h) GPS coordinate;
  i) Surface type;
  j) Installation depth;
  k) Original installation date or date of last maintenance if known;
  l) Ambient temperature;
  m) Surface condition (frozen, wet, dry);
  n) All G related readings from accelerometers;
  o) HIC score.

Figure 7:
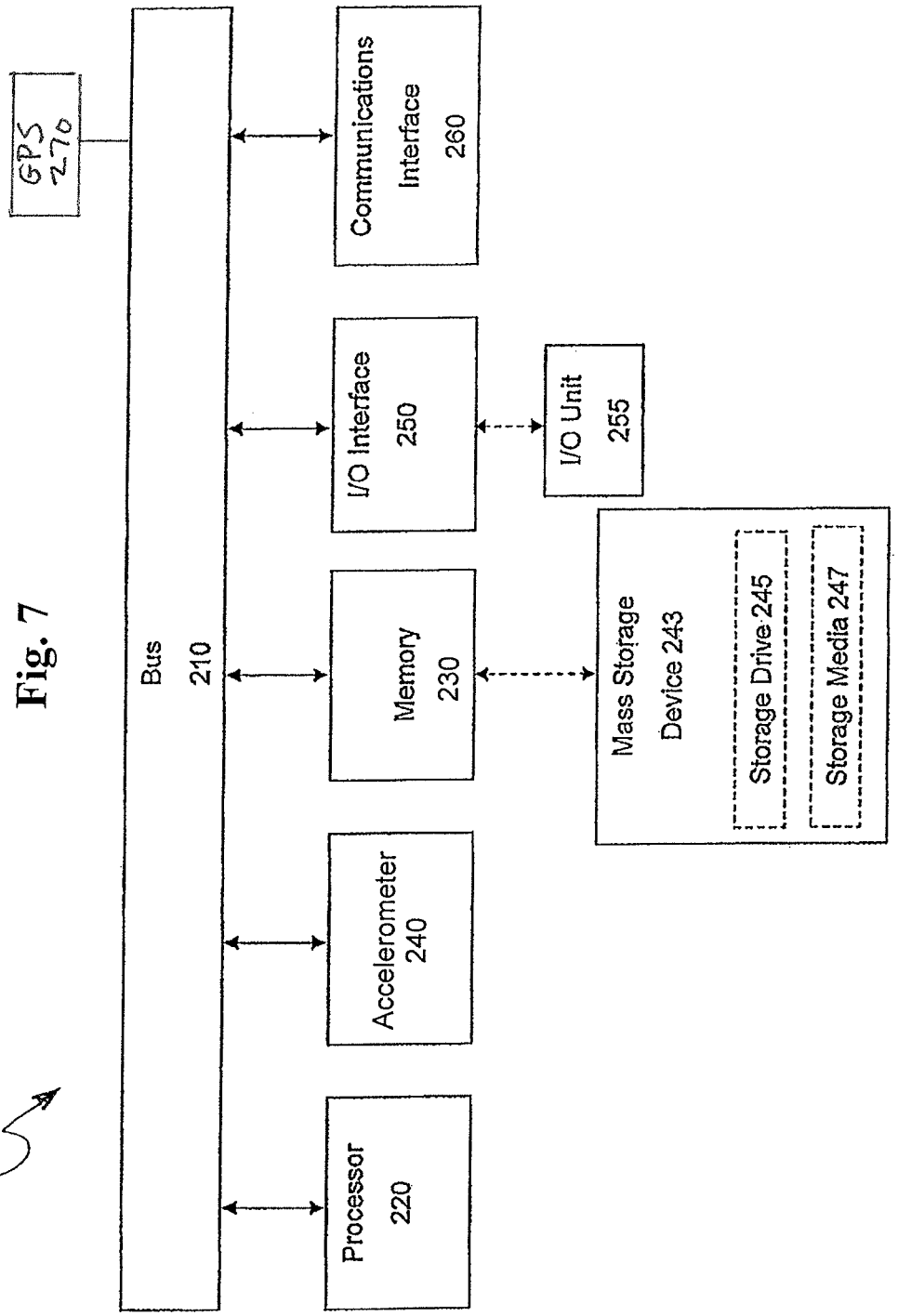
FIG. 7 is a functional block diagram of the system for testing the hardness or impact attenuation of a surface in accordance with the present disclosure.
Figure 9B:
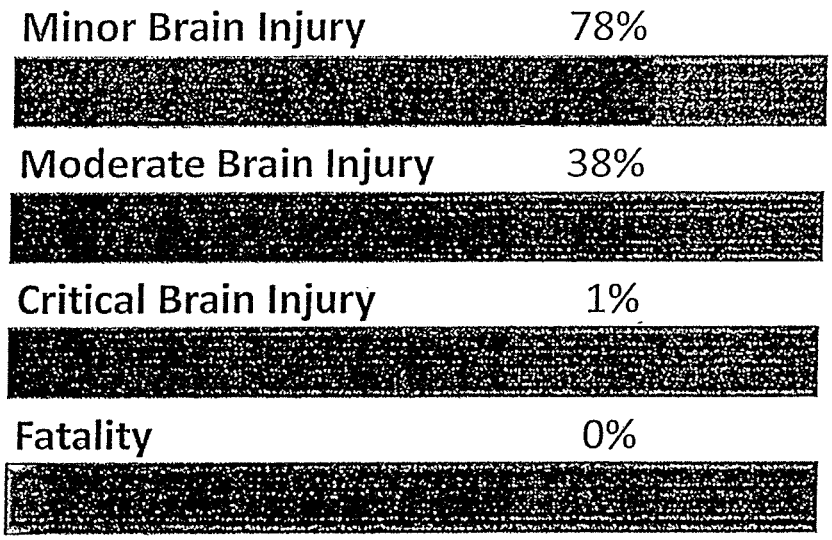

FIG. 7 illustrates a functional block diagram of an exemplary impact tester 10 that may be used to implement the apparatus, system and methods according to the present invention. The impact tester 10 may carry out the methods presented herein as computer code, or may transmit data to the HMI 20 for carrying out the methods disclosed herein.

As described above and further shown in FIG. 7, an example of an impact tester 10 system, in accordance with the disclosure herein, comprises one or more processors, such as processor 220, which may be a special purpose or a general-purpose processor and is connected to a bus 210. Bus 210 connects the processor 220 to various other components of the impact tester 10, but it is contemplated bus 210 may connect processor 220 to components (not shown) such as, additional sensors, battery and/or charging system, etc. The battery or batteries may be charged using a battery charger, a USB port, or other ways known in the industry. The batteries may also be replaced if necessary.

It is also contemplated that bus 210 connects the processor 220 to other computer systems either wirelessly or through a wired connection after testing has been performed. Via the bus 210, the processor 220 can receive computer code for programming or for updates, as understood by one having ordinary skill in the art. The term "computer code" includes, for example, programs, instructions, signals and/or data. The processor 220 executes computer code and may further send the computer code via the bus 210.

Impact tester 10 may include one or more memories, such as memory 230. It is contemplated that the memory 230 can function as a computer usable storage medium to store and/or access computer code. The memory 230 and a second memory (not shown) may be, for example, random access memory (RAM), read-only memory (ROM), a mass storage device, or any combination thereof.

In an embodiment, the memory 230, or an additional memory, can also be a mass storage device 243. The mass storage device 243 may comprises a storage drive 245 and a storage media 247. It is contemplated the storage media 247 may or may not be removable from the storage drive 245. Mass storage devices 243 with storage media 247 that are removable, otherwise referred to as removable storage media, also allow computer code and/or data to be transferred to and/or from the impact tester 10. Computer code can also be transferred to the impact tester 10 wirelessly or through a temporary wired connection.

A mass storage device 243 may include, for example, a Compact Disc Read-Only Memory ("CDROM"), ZIP storage device, tape storage device, magnetic storage device, optical storage device, Micro-Electro-Mechanical Systems ("MEMS"), nanotechnological storage device, floppy storage device, hard disk device. Mass storage device 243 also includes program cartridges and cartridge interfaces (such as that found in video game devices), removable memory chips (such as an EPROM, or PROM) and associated sockets.

FIG. 7 also shows that the impact tester 10 includes at least one accelerometer 240 connected to the bus 210 for acquiring data during testing and at other times. In the preferred embodiment, the impact tester utilizes four accelerometers as described herein. The accelerometers 240 can be connected to the processor 220 through the bus 210, may be connected directly to the processor 220 or may be integral to the processor 220, as understood by one having ordinary skill in the art.

The impact tester 10 may further or alternatively include other means for computer code to be loaded into or removed from the impact tester 10, for example, input/output ("I/O") interface 250 and/or communications interface 260. Both the I/O interface 250 and the communications interface 260 allow computer code to be transferred between the impact tester 10 and external devices including other computer systems. This transfer may be bi-directional or Omni-direction to or from the impact tester 10.

Computer code transferred by the I/O interface 250 and the communications interface 260 are typically in the form of signals, which may be electronic, electromagnetic, optical, or other signals capable of being sent and/or received by the interfaces. These signals may be transmitted via a variety of modes including, but not limited to, wire or cable, fiber optics, a phone line, a cellular phone link, infrared ("IR"), and radio frequency ("RF") link.

The I/O interface 250 may be any connection, wired or wireless, that allows the transfer of computer code. An I/O interface 250 includes, for example, an analog or digital audio connection, digital video interface ("DVI"), video graphics adapter ("VGA"), musical instrument digital interface ("MIDI"), parallel connection, PS/2 connection, serial connection, universal serial bus connection ("USB"), IEEE1394 connection, PCMCIA slot and card. In certain embodiments, the I/O interface 250 connects to an I/O unit 255, such as a user interface, monitor, speaker, printer, touch screen display, to name a few.

The communications interface 260 is also any connection that allows the transfer of computer code. Communication interfaces include, but are not limited to, a modem, network interface (such as an Ethernet card), wired or wireless systems (such as Wi-Fi, Bluetooth, IR), local area networks, wide area networks, intranets, etc.

The invention is also directed to computer products, otherwise referred to as computer program products, to provide software that includes computer code to the impact tester 10 or the HMI 20. Processor 220 executes the computer code in order to implement the methods of the present invention. As an example, the methods according to the present invention may be implemented using software that includes the computer code, wherein the software is loaded into the impact tester 10 using a memory 230 such as the mass storage drive 243, or through an I/O interface 250, communications interface 260, or any other interface with the impact tester 10. The computer code in conjunction with the impact tester 10 described herein may perform any one of, or any combination of, the steps of any of the methods presented herein. It is also contemplated that the methods according to the present invention may be performed automatically, or may be invoked by some form of manual intervention.

The impact tester 10 of FIG. 7 is provided only for purposes of illustration, such that the present invention is not limited to this specific embodiment. It is appreciated that a person skilled in the relevant art knows how to program and implement the invention using any computer system or network architecture.

While the disclosure is susceptible to various modifications and alternative forms, specific exemplary embodiments thereof have been shown by way of example in the drawings and have herein been described in detail. It should be understood, however, that there is no intent to limit the disclosure to the particular embodiments disclosed, but on the contrary, the intention is to cover all modifications, equivalents, and alternatives falling within the scope of the disclosure.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation given that such combination is not illogical or non-functional.

Although numerous embodiments of this invention have been described above with a certain degree of particularity, those skilled in the art could make numerous alterations to the disclosed embodiments without departing from the spirit or scope of this disclosure. All directional references (e.g., plus, minus, upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the any aspect of the disclosure. As used herein, the phrased "configured to," "configured for," and similar phrases indicate that the subject device, apparatus, or system is designed and/or constructed (e.g., through appropriate hardware, software, and/or components) to fulfill one or more specific object purposes, not that the subject device, apparatus, or system is merely capable of performing the object purpose. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A method of determining the impact attenuation of a surface for a playground or sports field utilizing a wireless, handheld impact tester in order to mitigate related injuries, the method comprising the steps of:
    a) allowing a user to select a location of a playground or sports field to test;
    b) providing the user with a wireless handheld impact tester, said wireless handheld impact tester comprising at least one multiaxis accelerometer and a communication system;
    c) providing the user with an application to receive data from the wireless handheld impact tester, said application loaded on a computing device;
    d) instructing the user to drop the wireless handheld impact tester on the surface of said playground or sports field from a height to be tested, said dropping the wireless handheld impact tester irrespective of rotation of said handheld impact tester and angle of impact with the ground;
    e) using the at least one multi axis accelerometer associated with said wireless handheld impact tester to obtain data pertaining to the impact attenuation of said surface of said playground or sports field during said drop of said wireless handheld impact tester; and
    f) allowing the wireless communication system associated with said wireless handheld impact tester to remotely transmit data pertaining to the impact attenuation of said surface of said playground or sports field back to said computing device in real time.

2. The method of determining the impact attenuation of a surface for a playground or sports field utilizing a wireless handheld impact tester in order to mitigate related injuries of claim 1, the method further comprising the steps of:

g) repeating steps d, e and f multiple times in different locations on the same surface of said playground or sports field;
h) generating results for each drop and for the multiple drops of the wireless handheld impact tester; and
i) displaying the results in real time for each drop and for the multiple drops on said computing device.

3. The method of determining the impact attenuation of a surface for a playground or sports field utilizing a wireless handheld impact tester in order to mitigate related injuries of claim 2, the method further comprising the step of:
j) transmitting said results in real time of the multiple drops to a central server for authenticity purposes.

4. The method of determining the impact attenuation of a surface for a playground or sports field utilizing a wireless handheld impact tester in order to mitigate related injuries of claim 2, wherein the results generated for each drop comprise one or more of the fall height of the wireless handheld impact tester from the height it was dropped to the ground at impact, the maximum velocity when the wireless handheld impact tester impacts the ground, the angle of impact, the maximum acceleration during impact, the rotation of the wireless handheld impact tester at impact, and the Head Impact Criteria (HIC).

5. The method of determining the impact attenuation of a surface for a playground or sports field utilizing a wireless handheld impact tester in order to mitigate related injuries of claim 1, wherein the data obtained comprises one or more of the time the wireless handheld impact tester begins to fall and the time it first impacts the ground.

6. The method of determining the impact attenuation of a surface for a playground or sports field utilizing a wireless handheld impact tester in order to mitigate related injuries of claim 1, further comprising the step of performing a diagnostic function in which the computing device checks for connectivity to the handheld impact tester.

7. The method of determining the impact attenuation of a surface for a playground or sports field utilizing a wireless handheld impact tester in order to mitigate related injuries of claim 1, further comprising the step of performing a diagnostic function in which the computing device prompts the wireless handheld impact tester to run a system diagnostic check to ensure one of proper battery level and proper function.

\* \* \* \* \*